(12) United States Patent
Rietzel

(10) Patent No.: US 7,978,817 B2
(45) Date of Patent: Jul. 12, 2011

(54) CARRYING OUT AND MONITORING IRRADIATION OF A MOVING OBJECT

(75) Inventor: Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 93 days.

(21) Appl. No.: 12/421,891

(22) Filed: Apr. 10, 2009

(65) Prior Publication Data

US 2009/0279662 A1 Nov. 12, 2009

Related U.S. Application Data

(60) Provisional application No. 61/045,310, filed on Apr. 16, 2008.

(30) Foreign Application Priority Data

Apr. 16, 2008 (DE) .......................... 10 2008 019 128

(51) Int. Cl.
*A61N 5/10* (2006.01)
*H05G 1/60* (2006.01)
*H05G 1/64* (2006.01)

(52) U.S. Cl. ............... 378/65; 378/22; 378/25; 378/197

(58) Field of Classification Search .................... 378/22, 378/25, 26, 42, 65, 197
See application file for complete search history.

(56) References Cited

U.S. PATENT DOCUMENTS

| | | | |
|---|---|---|---|
| 6,061,422 A * | 5/2000 | Miyazaki et al. ............... | 378/15 |
| 6,196,715 B1 * | 3/2001 | Nambu et al. ................. | 378/197 |
| 6,970,585 B1 * | 11/2005 | Dafni et al. .................... | 382/131 |
| 7,245,696 B2 | 7/2007 | Pang et al. | |
| 7,245,698 B2 * | 7/2007 | Pang et al. ...................... | 378/65 |
| 7,394,889 B2 * | 7/2008 | Partain et al. ................... | 378/37 |
| 7,519,151 B1 * | 4/2009 | Shukla et al. ................... | 378/65 |
| 7,532,705 B2 * | 5/2009 | Yin et al. ........................ | 378/65 |
| 7,567,647 B1 * | 7/2009 | Maltz ............................. | 378/21 |
| 7,664,221 B2 * | 2/2010 | Bruder ............................ | 378/4 |
| 7,711,087 B2 * | 5/2010 | Mostafavi ...................... | 378/65 |
| 2007/0010731 A1 | 1/2007 | Mistretta | |
| 2007/0025509 A1 | 2/2007 | Pang et al. | |
| 2007/0237290 A1 | 10/2007 | Mostafavi | |

FOREIGN PATENT DOCUMENTS

| | | |
|---|---|---|
| DE | 103 36 105 A1 | 4/2004 |
| DE | 10 2005 053 971 A1 | 5/2007 |
| DE | 10 2005 059 210 A1 | 6/2007 |
| EP | 1 479 411 A1 | 11/2004 |
| EP | 1 758 649 A1 | 3/2007 |
| WO | WO 02/22019 A1 | 3/2002 |

OTHER PUBLICATIONS

German Office Action dated Dec. 15, 2008 with English translation.
European Patent Office Report for co-pending Application No. EP 09 15 4947 dated Jul. 2009 with English translation.
European Patent Office Report for co-pending Application No. EP 09 15 4947 dated Sep. 10, 2009 with English translation.
European Patent Office Action for co-pending Application No. EP 09 154 947 dated Oct. 25, 2010 with English translation.

\* cited by examiner

*Primary Examiner* — Allen C. Ho
(74) *Attorney, Agent, or Firm* — Lempia Summerfield Katz LLC

(57) ABSTRACT

A system for carrying out or monitoring irradiation of a moving object using a particle beam is provided. A particle beam may be directed onto the moving object from a beam outlet. X-ray images from different directions are recorded by an imaging unit. The imaging unit may include an x-ray detector and an x-ray emitter opposite the x-ray detector. The imaging unit may be positioned around the object independently of the position of the beam outlet, for example, during application of the particle beam. The X-ray images may be used to reconstruct a series of digital tomosynthesis images of the moving object online. The reconstructed digital tomosynthesis images are evaluated so that movement of the moving object is captured and the irradiation profile is controlled.

18 Claims, 3 Drawing Sheets

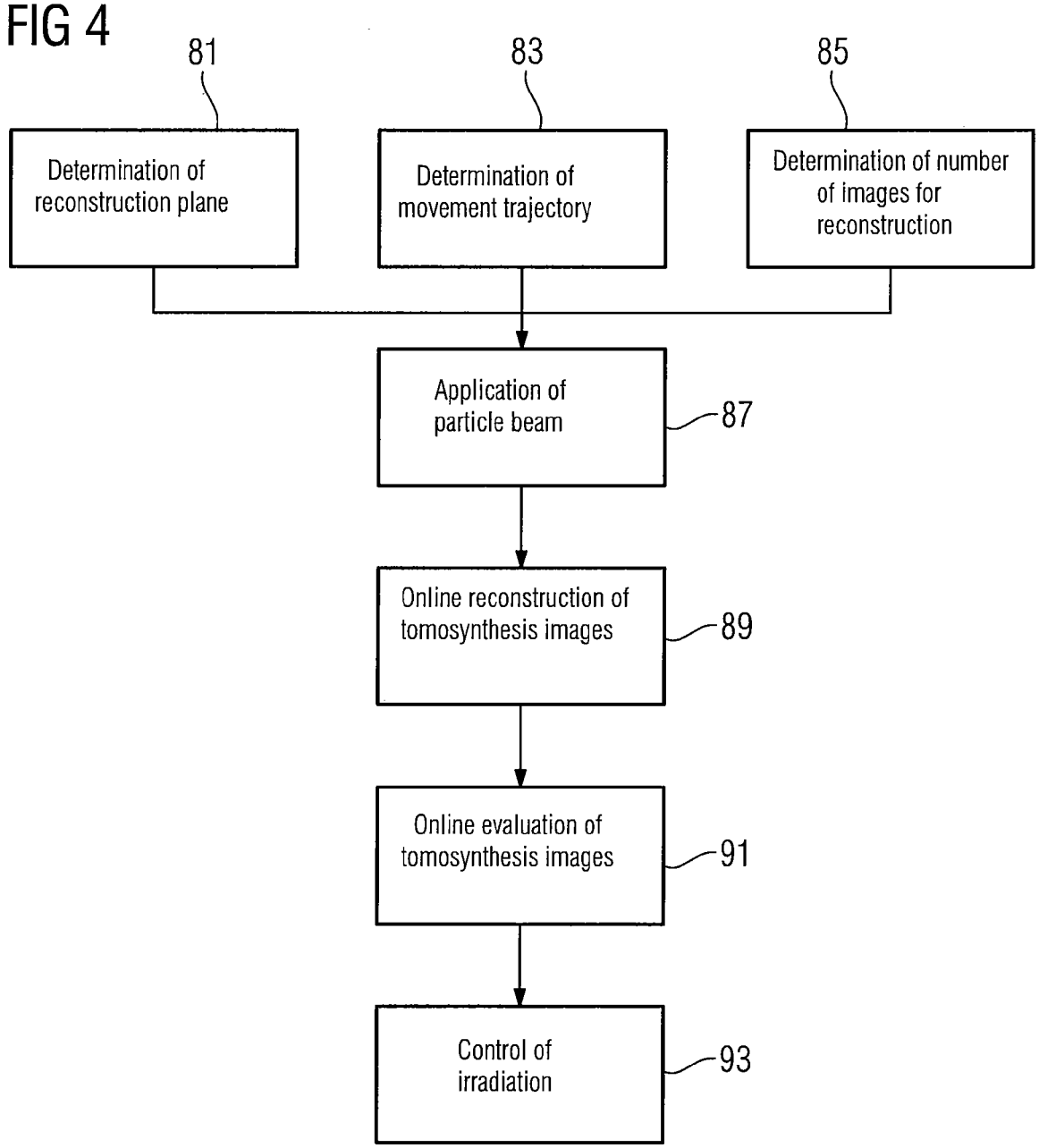

CARRYING OUT AND MONITORING IRRADIATION OF A MOVING OBJECT

This patent document claims the benefit of DE 10 2008 019 128.0, filed Apr. 16, 2008, which is hereby incorporated by reference. This patent document also claims the benefit of U.S. provisional application 61/045,310, filed on Apr. 16, 2008, which is also hereby incorporated by reference.

BACKGROUND

The present embodiments relate to carrying out and monitoring irradiation of a moving object.

Radiation therapy includes irradiating diseased tissue with x-ray beams, electron beams, or particle beams. Particle therapy is used to treat tissue, such as tumors. Irradiation methods, as deployed in particle therapy, can also be deployed in non-therapeutic areas. For example, irradiation methods may be used in research work (e.g., the irradiation of phantoms or non-living bodies) or the irradiation of materials.

Particles are generated during particle therapy. The particles may be ions, such as protons, carbon ions, or other types of ions. The particles are accelerated to high energies in an accelerator, formed into a particle beam, and then directed onto the tissue to be irradiated. The particles penetrate into the tissue to be irradiated and discharge the particle's energy in a circumscribed region. The depth of penetration of the particle beam into the tissue is a function of the energy of the particle beam. The greater the energy of the particle beam, the deeper the particles penetrate into the tissue to be irradiated.

Movement of the object to be irradiated is taken into account during irradiation. Respiratory movements, for example, can result in a significant change in the position of lung and liver tumors. As a result, the target volume may not be irradiated as desired. During intensity-modulated irradiation, there can be interference effects between the irradiation and the target volume movement. Accordingly, a scheduled dosed application to the target volume is impeded.

Different methods are known for controlling the irradiation profile with moving target volumes. For example, gating includes directly or indirectly capturing the movement of the target volume. Irradiation of the target volume then only takes place when the target volume is in a desired location. Tracking may include tracking of the particle beam.

The movement of the target volume can be captured using different methods, for example, using external markers on the patient, by observing the surface of the patient, or using belts or spirometers that capture the respiratory movement. Another option is to continuously record x-ray images or fluoroscopy images of the object. This allows the movement of the object to be captured internally. Possible errors due to differences between external and internal movement can be avoided.

U.S. Pat. No. 7,245,698 B2 discloses a system for irradiating with x-ray beams. The system reconstructs digital tomosynthesis recordings of the object.

SUMMARY AND DESCRIPTION

The present embodiments may obviate one or more of the drawbacks or limitations inherent in the related art. For example, in one embodiment, a method for carrying out an irradiation treatment using a particle beam is provided. The method may be used to capture possible movement of the object to be irradiated in a flexible and precise manner. In another example, a method for monitoring an irradiation treatment is provided.

In one embodiment, a device for carrying out irradiation of a moving object with a treatment beam includes a beam outlet, an imaging unit, and a control unit. A treatment beam, such as a particle beam accelerated to irradiation energy, can be directed onto the moving object from the beam outlet. The imaging unit may include an x-ray detector and an x-ray emitter opposite the x-ray detector. The imaging unit may be positioned around the object independently of the position of the beam outlet. The imaging unit may be configured to record x-ray images from different directions during an application of the treatment beam and to reconstruct a series of digital tomosynthesis images of the moving object from these online. The control unit may be configured to evaluate the digital tomosynthesis images in the series and to control the irradiation profile based on the evaluation of the digital tomosynthesis images.

Digital tomosynthesis images are two-dimensional images that have good contrast for soft part tissue compared to the contrast of x-ray images, such as fluoroscopy images. Two-dimensional images may be used to generate a three-dimensional image data record, for example, during the reconstruction. The two-dimensional images include a sharp image in one plane, in contrast to three-dimensional image data records, for example, from cone beam computed tomography. With such a three-dimensional data record the desired soft part contrast is reproduced in this plane in the image. The other planes in the three-dimensional data record then have poor image quality. It is possible to capture a movement of the moving object by evaluating the digital tomosynthesis images. It is also possible to capture movement of soft parts, for example, compared with conventional x-ray images. The captured movement of a target volume can then be used to control the irradiation profile. Conventional x-ray images are used to capture high-contrast objects such as bones.

In contrast to the generation of three-dimensional image data records, for example, by so-called cone beam computed tomography, the recording of x-ray images for the reconstruction of digital tomosynthesis images and the reconstruction of the tomosynthesis images is considerably quicker because data only has to be recorded over a smaller angle range. The temporal resolution that can be achieved with two-dimensional digital tomosynthesis images for tracking the movement of an object to be irradiated is significantly higher. The two-dimensional digital tomosynthesis images are particularly suitable for capturing the actual (e.g., the current) movement of the object.

In one example, when irradiating liver or lung tumors, the tumor and/or the tumor's movement may be captured directly. The irradiation profile may be controlled on the basis of the tumor's movement. This information results in more precise capturing of the tumor movement. Irradiation is tailored to (based on) the movement of the tumor. As a result, greater irradiation precision is possible. The advantages can be of significant importance for lung and liver tumors in particular, as the tumors can be visualized directly during irradiation.

The irradiation profile may be controlled in such a manner that irradiation is interrupted (gating), for example, when the object to be irradiated moves too far away from a predefined setpoint position. Alternatively and/or additionally, the direction of the particle beam and/or the penetration depth of the particle beam can be adjusted accordingly at a later stage by deflecting the particle beam and/or adjusting the energy of the particle beam, so that the particle beam tracks the movement of the object to be irradiated.

The x-ray detector and x-ray emitter can be pivoted, for example, during the continuous movement. The x-ray detector and x-ray emitter can execute more radical, for example, more complex and recurrent, movements.

During the entire process and/or during application of the particle beam, the position of the beam outlet can remain spatially fixed, as the imaging unit can be positioned independently of the beam outlet. Positioning of the imaging unit may not be related to the position of the beam outlet. As a result, the device may be flexibly configured. The device may be deployed in an irradiation chamber that has a spatially fixed beam outlet. Alternatively, the device may be deployed in an irradiation chamber in which the beam outlet may be moved into various positions by a gantry. The beam outlet may remain spatially fixed an irradiation chamber during application of the particle beam.

During online reconstruction of the digital tomosynthesis images, a temporal series of the digital tomosynthesis images results. The current movement of the moving object is mapped in the temporal series of the digital tomosynthesis images. During the reconstruction of one of the tomosynthesis images, it is possible to use, for example, "n" essentially successive x-ray images, which were recorded from different directions. As used herein, "n" indicates a number of x-ray images required to allow the required quality of tomosynthesis. The higher the number "n," the more raw data is available for the tomosynthesis image, so the quality of the tomosynthesis image may be enhanced. The higher the number "n," however, the lower the temporal resolution displayed by the tomosynthesis image because the associated x-ray images were recorded over a longer time period. A compromise may be selected, which provides the desired tomosynthesis quality and the desired temporal resolution.

Reconstruction of the tomosynthesis images may be continuous, based on the required number "n" of x-ray images, for example, projections, in each instance. The different tomosynthesis images do not have to be independent with respect to the raw data (e.g., x-ray images). For example, to reconstruct a tomosynthesis image, "n" successive x-ray images are used as raw data. During the reconstruction of the subsequent tomosynthesis image, one or more temporally consecutive x-ray images can be added to the "n" successive x-ray images, with the same number of x-ray images being deleted from the start of the successive x-ray images. If the x-ray detector and x-ray emitter rotate in a circular manner, for example, around the particle beam, the required number "n" of images may be taken from a ring buffer.

In one embodiment, the imaging unit is configured to move the x-ray detector and/or the x-ray emitter opposite the x-ray detector in a spiral or circular manner in a precession movement. For example, the axis of the x-ray beam may execute a circular or spiral precession movement. This allows x-ray images to be recorded from a large number of different spatial directions. Since a circular or spiral precession movement is generally regular, it is simple to implement continuous online reconstruction of the tomosynthesis images, as it is possible to utilize the regularity of the movement.

In one embodiment, a number of x-ray images used to reconstruct one of the tomosynthesis images may be tailored to the movement of the object. The movement of the object may include an actual movement or an anticipated movement, for example, based on empirically established values or prior testing. Alternatively or additionally, the speed at which the x-ray detector and x-ray emitter are moved around the object may be tailored to the movement of the object. For example, when the object is moving more quickly, the speed of the x-ray detector and x-ray emitter may be increased to achieve adequate temporal resolution despite the faster object movement.

In another embodiment, the reconstruction plane, along which at least one of the tomosynthesis images is reconstructed, may be freely selected. The positioning of the x-ray detector and the x-ray emitter may be adjusted correspondingly as the image data is being recorded. The reconstruction plane may be positioned so that movement of the target object may be optimally captured. For example, the reconstruction plane may be selected so that the spatial direction of movement of the object lies in the reconstruction plane. This allows object movement to be determined particularly efficiently by evaluating the tomosynthesis images in the reconstruction plane.

The x-ray detector and the x-ray emitter opposite the x-ray detector may be disposed on a support arm, which can be positioned in the chamber by a robotic positioning system. As a result, the imaging unit may be flexibly positioned in the chamber. The robotic positioning system may permit very fast movement of the x-ray detector and the x-ray emitter, so that fast movements of the object may be captured reliably and precisely.

In one embodiment, a method for monitoring an irradiation treatment of a moving object using a treatment beam is provided. The method may include recording x-ray images from different directions of the moving object during application of a treatment beam from a fixed spatial direction, direct online reconstruction of a series of digital tomosynthesis images from the recorded x-ray images, capturing the movement of the moving object by evaluating the digital tomosynthesis images, and controlling the irradiation profile as a function of the captured movement.

The method may include the features discussed above for the device.

BRIEF DESCRIPTION OF THE DRAWINGS

FIG. 4 illustrates one embodiment of a method for controlling irradiation.

DETAILED DESCRIPTION

Figure 1:
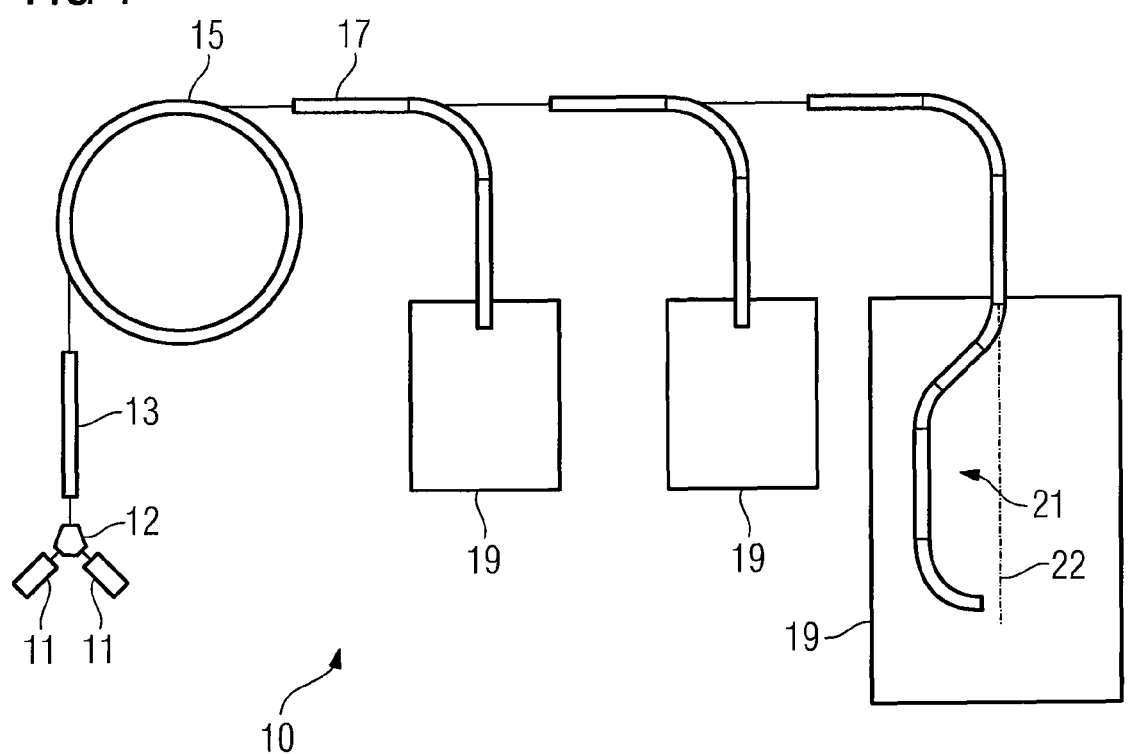
FIG. 1 illustrates one embodiment of a particle therapy unit.

FIG. 1 shows a particle therapy unit 10. The particle therapy unit 10 may be used for the irradiation of a body, such as a tumorous tissue, using a particle beam.

The particles may be ions, such as protons, pions, helium ions, carbon ions or other types of ion, for example. The particles may be generated in a particle source 11. Two particle sources 11 may generate two different types of ions, as shown in FIG. 1. It is possible to switch between the two types of ion within a short time interval. A solenoid 12, for example, is used for switching. The solenoid 12 may be disposed between the ion sources 11 and an accelerator 13. The particle therapy unit 10 may be operated, for example, with protons and carbon ions at the same time.

The ions generated by the one or more ion sources 11 and optionally selected using the solenoid 12 are accelerated to a first energy level in the pre-accelerator 13. The pre-accelerator 13 is a linear acceleration (LINAC for LINear ACcelerator). The particles are then fed into an accelerator 15, for example, a synchrotron or cyclotron. In the accelerator 15, the particles are accelerated to high energies, as required for irradiation. After the particles leave the accelerator 15, a high-energy beam transportation system 17 channels the particle beam to one or more irradiation chambers 19. In an irradiation chamber 19, the accelerated particles are directed onto a body to be irradiated. This may be done from a fixed direction (in a fixed beam chamber) or from different directions by way of a rotatable gantry 21 that can be moved about an axis 22.

Other particle therapy units may be used. The exemplary embodiments described below can be deployed both in conjunction with the particle therapy unit illustrated with reference to FIG. 1 and also with other particle therapy units.

Figure 2:
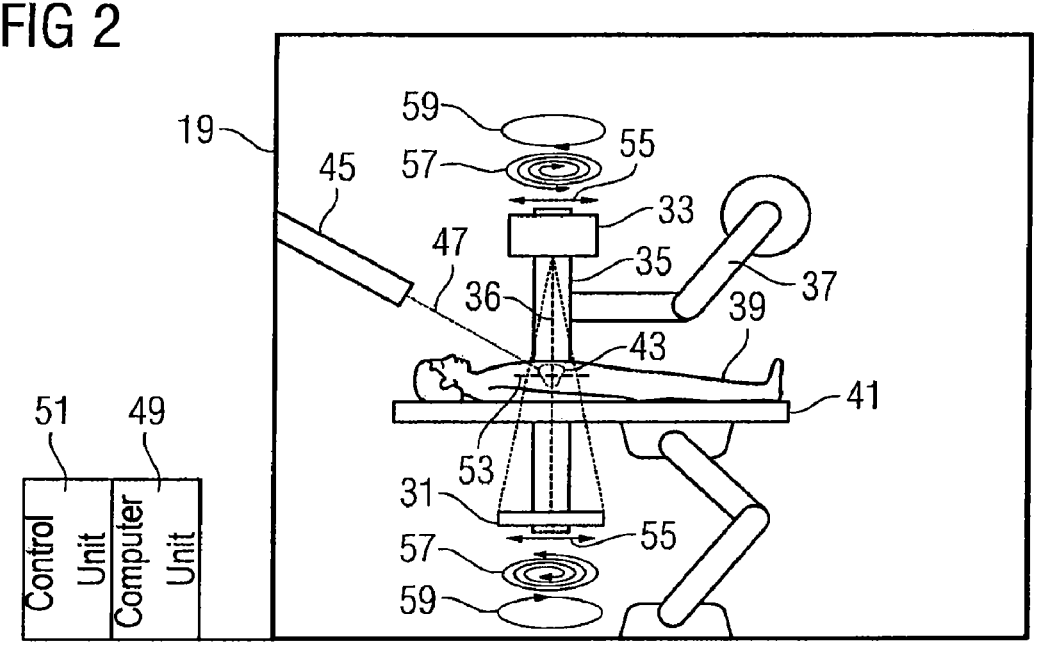
FIG. 2 illustrates one embodiment of a beam outlet and an imaging unit in an irradiation chamber.

FIG. 2 shows a possible arrangement of a beam outlet and the imaging unit in an irradiation chamber.

The imaging unit may include an x-ray detector 31 and an x-ray emitter 33, which are disposed opposite one another on a support arm 35. The support arm 35 may be a C-arm. The support arm 35 may be positioned in a flexible manner in the chamber with a robot arm 37, for example, with a six-axis elbow-arm robot. The x-ray detector 31 and x-ray emitter 33 may be used to record x-ray recordings, for example, fluoroscopy recordings, of a patient 39, who is positioned on a patient couch (support) 41 for irradiation purposes. The target volume 43, for example, an organ, may be mapped in the fluoroscopy recordings.

As an alternative to the variant with the support arm, the x-ray detector and x-ray emitter may be positioned independently of one another, for example, using two robot arms. Positioning the x-ray detector and x-ray emitter may provide greater flexibility as there is no rigid support arm disposed between the x-ray emitter and the x-ray detector.

In one embodiment, one of the x-ray detector or the x-ray emitter may be positioned in a movable manner and the other may be positioned in a static position. For example, the x-ray detector may move and a movable shutter at the x-ray emitter can ensure that the x-ray beams are masked in a different manner.

A particle beam 47 may exit from a beam outlet 45 and may be directed onto the patient 39. A beam outlet 45 that is installed in a spatially fixed manner in the chamber is shown here. Alternatively it is also possible to secure the beam outlet 45 to a rotatable gantry so that the beam outlet 45 can be rotated around the patient 39. During application of the particle beam 47 however the beam outlet 45 generally remains in a fixed position.

The x-ray detector 31 and the x-ray emitter 33 can be positioned independently of the beam outlet 45. During application of the particle beam 47, the support arm 35 is moved by the robot arm 37, with a series of fluoroscopy images being recorded in the process. A series of digital tomosynthesis images is reconstructed online (also referred to as "on the fly" reconstruction) from the series of fluoroscopy images. In other words, a series of digital tomosynthesis images are reconstructed during application of the particle beam 47. The recorded fluoroscopy images are forwarded to a computer unit 49, in which reconstruction of the tomosynthesis images takes place.

The movement of the target volume 43 in the series of digital tomosynthesis images may be evaluated, for example, during application of the particle beam 47. The evaluation may take place "on the fly". The information may be obtained to control the irradiation profile. Evaluation and control of the irradiation profile may take place in a control unit 51. For example, the particle beam 47 may be switched off, as soon as the target volume 43 to be irradiated is no longer in a desired position and may be switched back on again as soon as the target volume 43 to be irradiated is back in the desired position. Alternatively and/or additionally, the particle beam 47 may track a movement of the target volume 43, when the movement of the target volume 43 takes place within certain limits.

The control unit 51 and/or the computer unit 49 for image reconstruction may be implemented in a single computer unit or can be split between different sub-units. The sub-units may be implemented as independent units or in a control unit for the particle therapy unit as a whole.

When the support arm 35 is positioned roughly vertically, as shown in FIG. 2, the reconstruction plane 53 of the tomosynthesis images lies roughly perpendicular to the support arm 35, in other words in a horizontal direction. Depending on the target volume to be mapped or its movement, another position of the reconstruction plane 53 may be selected. The reconstruction plane 53 should be selected so that the movement of the organ may be captured and resolved as effectively as possible.

The support arm 35 may be moved in different ways. A simple movement is shown by a double arrow 55 and may correspond to a pivoting movement. Another option for moving the support arm 35 is a circular or spiral movement, shown by the spiral 57 or the circle 59. The x-ray beam axis 36 may execute a precession movement.

Figure 3:
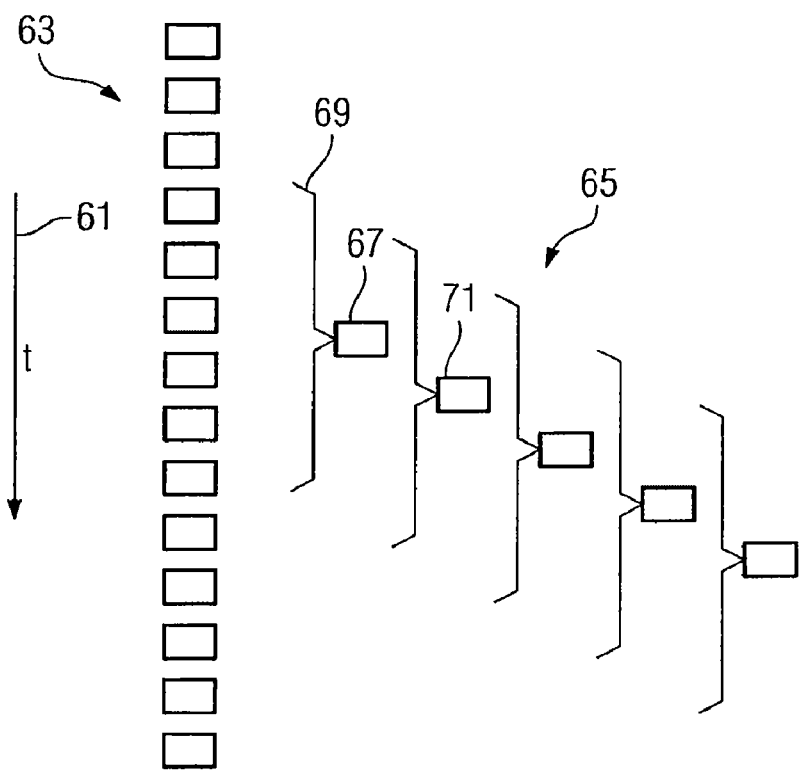
FIG. 3 illustrates one embodiment of online reconstruction of a temporal series of digital tomosynthesis images from a temporal series of x-ray images.

FIG. 3 shows how a temporal series of digital tomosynthesis images 65 is reconstructed from the temporal series of fluoroscopy images 63. The temporal profile is shown by the arrow 61.

In order to reconstruct a first tomosynthesis image 67, for example, a first group 69 of "n" successive fluoroscopy images is used. A cross-section through the organ to be mapped is mapped at a first time in the first tomosynthesis image 67. The actual reconstruction of the tomosynthesis image 67 from the first group 69 of "n" successive fluoroscopy images recorded from different directions can take place using known methods.

To reconstruct the next, temporally successive tomosynthesis image 71, one (or a number of) successive fluoroscopy image(s) is/are added to the first group 69 of "n" successive fluoroscopy images, while the same number of temporally older fluoroscopy images is deleted. The next tomosynthesis image 71 maps a cross-section through the organ at a later time. By continuing in this manner it is possible to produce a temporal series of tomosynthesis images 65 from the temporal series of fluoroscopy images 63. The tomosynthesis images 65 are not (or do not have to be) independent of one another with respect to their raw data (i.e., their fluoroscopy images 63).

The temporal resolution of the tomosynthesis images 65 or the precision of mapping in the tomosynthesis images 65 may be a function of the speed at which the fluoroscopy images 63 are recorded, the speed of direction change when recording the fluoroscopy images 63, the number "n" of fluoroscopy images used for the reconstruction, or other factors. These parameters may be tailored to requirements in each instance.

FIG. 4 shows a schematic overview of a method for controlling irradiation.

A spatial position of the reconstruction plane is determined (act 81). The reconstruction plane may be selected so that organ movement is captured as effectively as possible in the reconstruction plane. The beam outlet and the positioning of the imaging unit may not be related to one another spatially.

A movement trajectory of the x-ray detector and the x-ray emitter is also determined (act 83), for example, the spatial profile of the movement trajectory and/or the speed of movement. The speed of movement of the imaging device may be tailored to (based on) the movement of the organ. The movement of the organ may, for example, be the actual movement of the organ, measured using a suitable device, or the anticipated movement, which occurs typically with the organ. This allows a desired temporal resolution to be achieved during subsequent reconstruction of the tomosynthesis images.

The number of fluoroscopy images used for the reconstruction of one of the tomosynthesis images is also determined (act 85). The number of fluoroscopy images may be tailored to the movement trajectory and/or movement speed of the x-ray detector and the x-ray emitter, the desired precision of the reconstruction and/or in particular the movement of the organ to be mapped.

The reconstruction plane, movement trajectory, and/or number of fluoroscopy images for the reconstruction can be determined interactively, for example, by a user. Parameter settings may be used. The parameter settings may be stored previously. For example, it is possible to use a specific parameter setting during irradiation of a specific organ such as the lungs and to use another parameter setting during irradiation of another organ, such as the prostate gland, and so on. Patient-specific settings used during recurrent irradiation sessions may be used. Values tailored to requirements are stored respectively in the parameter settings.

Application of the particle beam (act 87) takes place during subsequent irradiation. As this application takes place, a temporal series of fluoroscopy images is recorded from different directions using the x-ray emitter and the x-ray detector. Reconstruction of a temporal series of digital tomosynthesis images (act 89) takes place online (or "on the fly"), in other words during application of the particle beam. Evaluation of the temporal series of digital tomosynthesis images allows the movement of the organ to be irradiated to be captured (act 91). The captured movement is used to control the irradiation profile (act 93).

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A device for carrying out irradiation of a moving object, the device comprising:
    a beam outlet configured to direct a treatment beam onto the moving object,
    an imaging unit comprising an x-ray detector and an x-ray emitter opposite the x-ray detector, the imaging unit being operable to be positioned around the moving object independently of a position of the beam outlet, the imaging unit being configured to record x-ray images from different directions by moving the imaging unit relative to the position of the beam outlet, the moving and the recording occurring during application of the treatment beam,
    a computer unit configured to reconstruct a series of digital tomosynthesis images of the moving object from the recorded x-ray images, the reconstruction being performed online, and
    a control unit configured to evaluate at least some of the digital tomosynthesis images and to control an irradiation profile based on the evaluation.

2. The device as claimed in claim 1, wherein the imaging unit is configured to carry out a movement, during which the x-ray emitter and an axis of an x-ray beam emitted by the x-ray emitter move in a circular or spiral precession movement.

3. The device as claimed in claim 2, further comprising at least one robot arm operable to position the x-ray detector or the x-ray emitter in a chamber.

4. The device as claimed in claim 1, wherein a number of x-ray images used to reconstruct one of the digital tomosynthesis images is based on an actual movement or an anticipated movement of the moving object.

5. The device as claimed in claim 1, wherein the x-ray detector and x-ray emitter are configured to be moved around the moving object at a speed that is based on an actual movement or an anticipated movement of the moving object.

6. The device as claimed in claim 1, wherein at least one of the digital tomosynthesis images is reconstructed along a selected reconstruction plane through the moving object.

7. The device as claimed in claim 5, wherein selection of the reconstruction plane is based on a spatial direction of an actual movement or an anticipated movement of the moving object.

8. The device as claimed in claim 1, wherein the imaging unit further comprises a support arm, the x-ray detector and the x-ray emitter being disposed on the support arm.

9. The device as claimed in claim 1, further comprising at least one robot arm operable to position the x-ray detector and the x-ray emitter.

10. The device as claimed in claim 1, wherein the treatment beam is a particle beam, and the beam outlet remains in a fixed position spatially during application of the particle beam.

11. A method for monitoring an irradiation treatment of a moving object using a treatment beam, the method comprising:
    recording x-ray images of the moving object from different directions by moving an imaging unit relative to an axis of the treatment beam, the recording and the moving occurring during application of the treatment beam from a fixed spatial direction;
    reconstructing, by a computer unit, a series of digital tomosynthesis images from the recorded x-ray images, the series of digital tomosynthesis images being reconstructed online;
    capturing a movement of the moving object by evaluating the series of digital tomosynthesis images; and
    controlling an irradiation profile of the treatment beam as a function of the captured movement.

12. The method as claimed in claim 11, further comprising moving an x-ray detector and an x-ray emitter in a circular or spiral precession movement about the moving object while the x-ray images are being recorded from different directions.

13. The method as claimed in claim 11, wherein reconstructing includes reconstructing at least one of the digital tomosynthesis images as a function of an actual movement or an anticipated movement of the moving object.

14. The method as claimed in claim 11, further comprising moving an x-ray detector and an x-ray emitter around the moving object during recording of the x-ray images from different directions, a speed at which the x-ray detector and the x-ray emitter are moved being tailored to an actual movement or an anticipated movement of the object.

15. The method as claimed in claim 11, further comprising selecting a reconstruction plane along which at least one of the digital tomosynthesis images is reconstructed.

16. The method as claimed in claim 15, wherein selecting the reconstruction plane includes selecting the reconstruction plane as a function of a spatial direction of an actual movement or an anticipated movement of the moving object.

17. The method as claimed in claim 11, wherein the treatment beam is a particle beam.

18. A method for monitoring an irradiation treatment of a moving object using a treatment beam, the method comprising:
recording x-ray images of the moving object from different directions during application of a treatment beam from a fixed spatial direction;
moving an x-ray detector and an x-ray emitter in a circular or spiral precession movement about the moving object while the x-ray images are being recorded from the different directions;
reconstructing, by a computer unit, a series of digital tomosynthesis images from the recorded x-ray images, the series of digital tomosynthesis images being reconstructed online;
capturing a movement of the moving object by evaluating the series of digital tomosynthesis images; and
controlling an irradiation profile of the treatment beam as a function of the captured movement.

* * * * *